United States Patent [19]

Grier

[11] Patent Number: 4,629,454
[45] Date of Patent: Dec. 16, 1986

[54] HYPODERMIC SYRINGE

[76] Inventor: Dale C. Grier, 10850 Slater Ave. NE., Kirkland, Wash. 98033

[21] Appl. No.: 717,535

[22] Filed: Mar. 29, 1985

[51] Int. Cl.⁴ ............................................ A61M 5/315
[52] U.S. Cl. .................................................. 604/229
[58] Field of Search ............... 604/229, 228, 218, 136, 604/134, 135, 202, 232, 241

[56] References Cited

U.S. PATENT DOCUMENTS 3,618,603 11/1971 Levenson ............................ 604/229
4,216,771 8/1980 Arlers .................................. 604/229

Primary Examiner—John D. Yasko
Attorney, Agent, or Firm—Delbert J. Barnard

[57] ABSTRACT

A squeezing finger pressure is exerted on a trigger (100) carried by a finger-grip body (12) of a hypodermic syringe (10). The depressed trigger (100) displaces the free end of a cantilever spring (34) inwardly, moving a lock element (88) out from a radial opening (90) in a sidewall portion of the finger-grip body (12). This frees a compression spring (78) allowing it to drive an internal bushing (14), of which the cantilever beam spring (24) is a part, against a cartridge (28) within a barrel portion (16) of the syringe (10). The cartridge (28) carries a needle (18) at its forward end. The needle is moved into tissue in which an injection is to be made. A plunger (20) is moved against a piston (42) within the cartridge (28) to cause injection. The plunger (20) includes a penetrator rod (58) at its forward end. The penetrator rod (58) is of such a length in diameter that when it is fully pushed into the piston (42) it causes a forward portion of the piston (42) to distort and bulge forwardly, displacing liquid from the cartridge (28) as it moves. When pressure is removed from the plunger (20), the forward portion of the piston (42) relaxes and moves rearwardly, creating an aspirating action within the cartridge (28).

25 Claims, 12 Drawing Figures

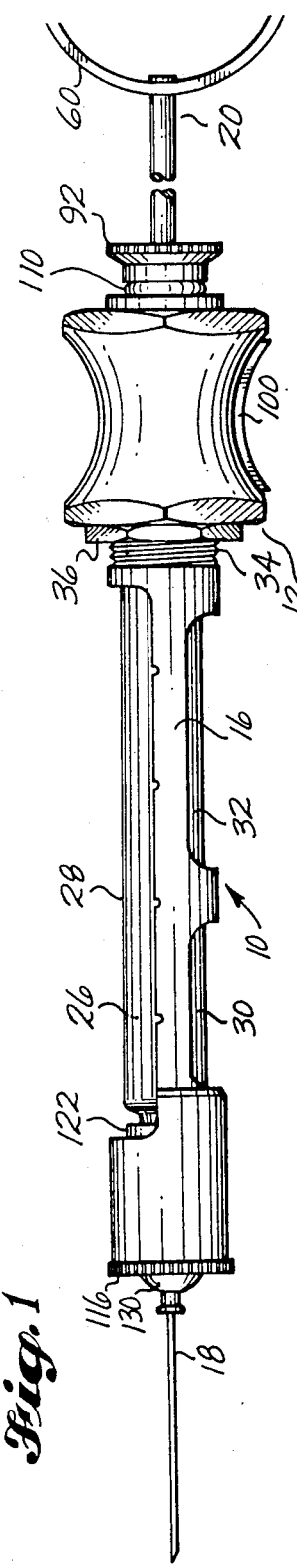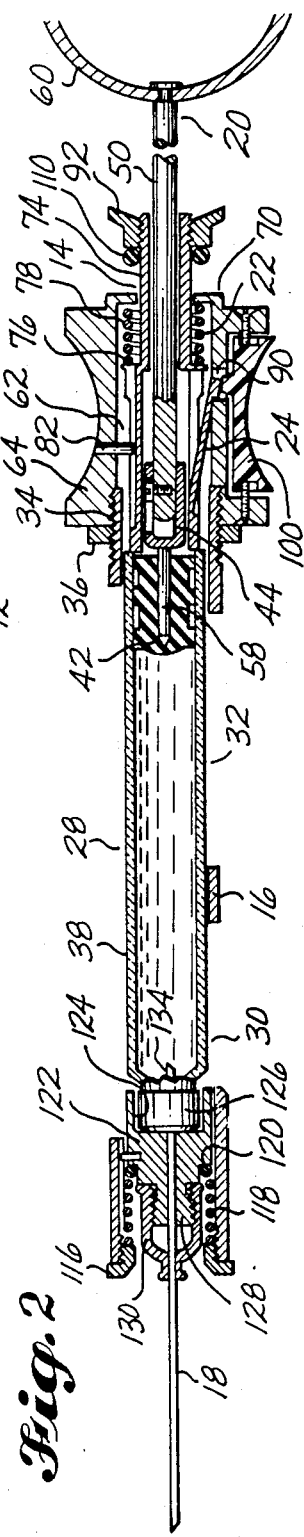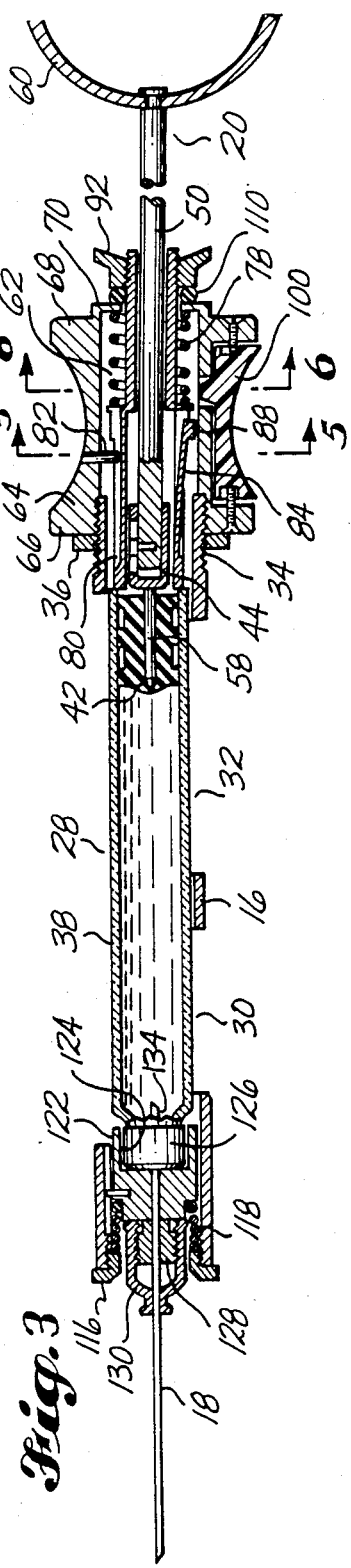

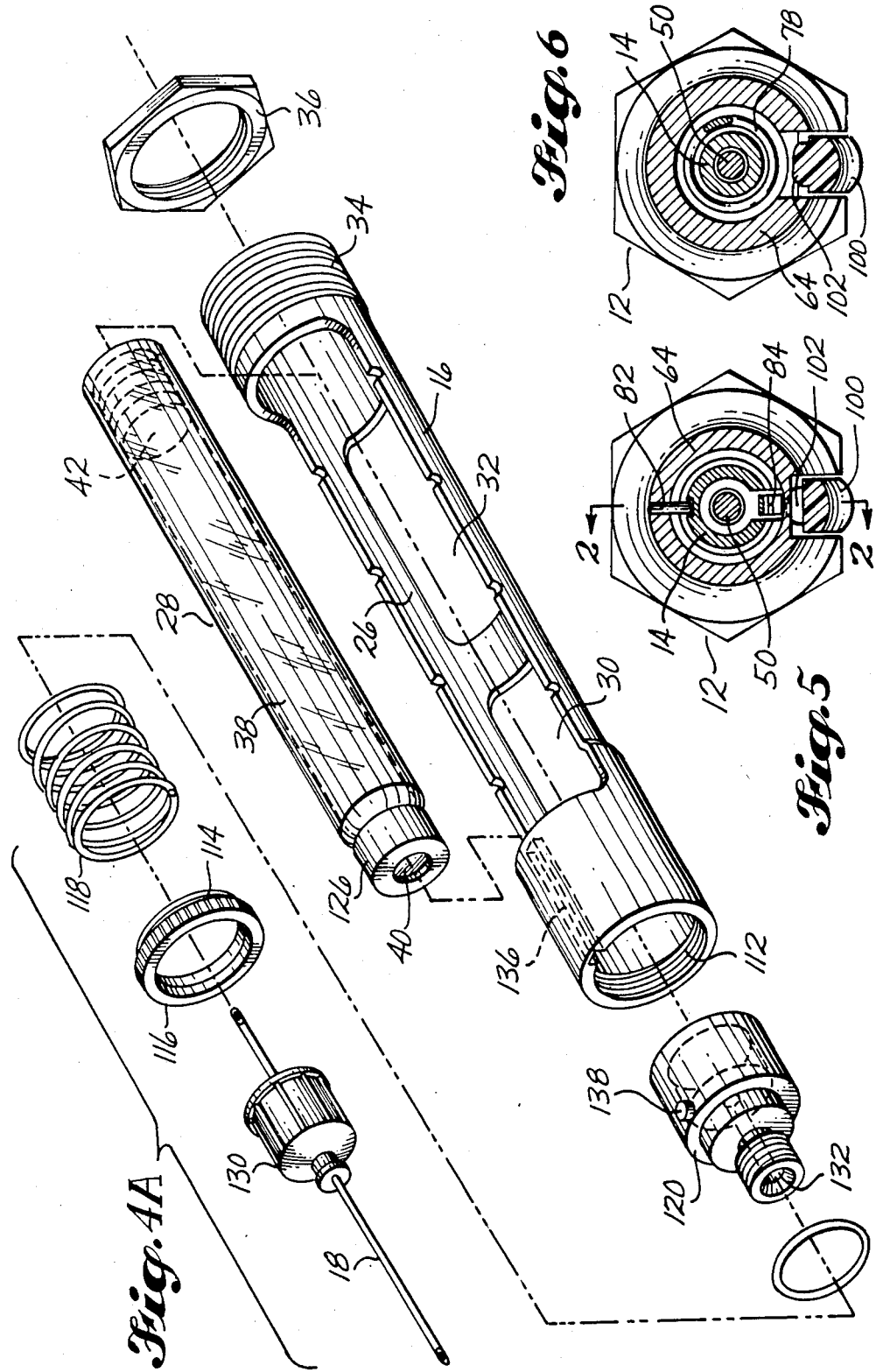

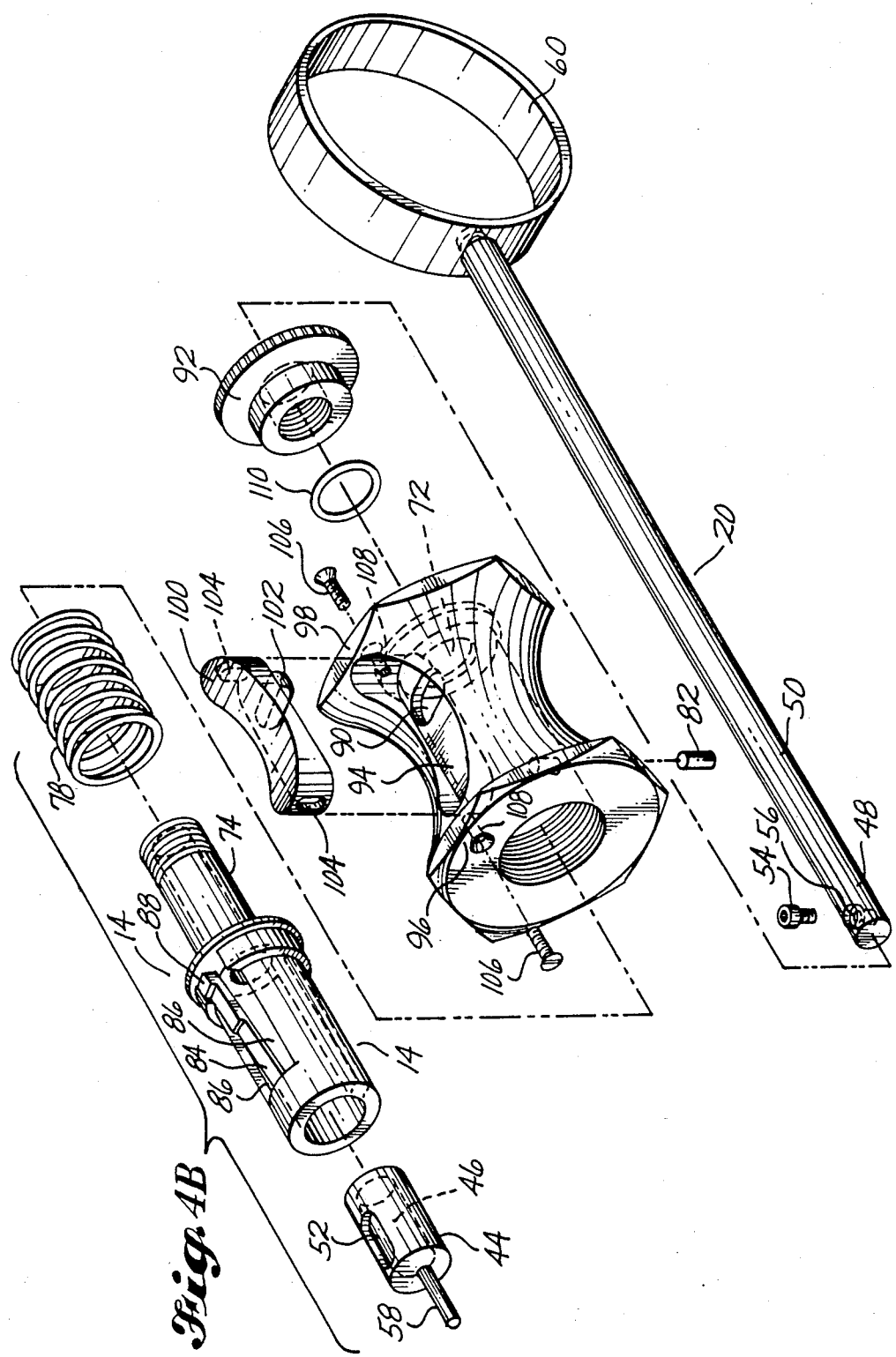

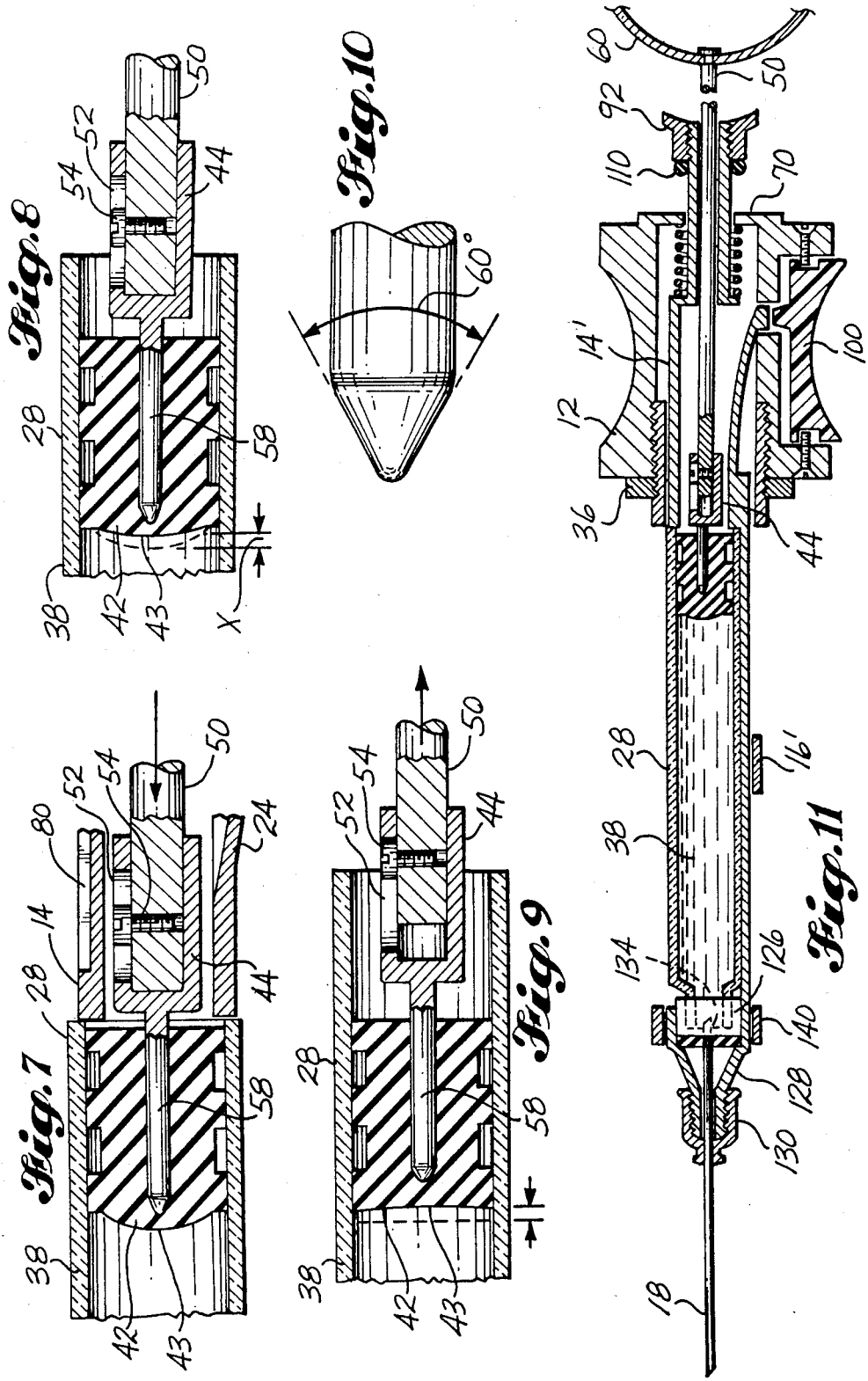

HYPODERMIC SYRINGE

TECHNICAL FIELD

This invention relates to hypodermic syringes. More particularly, it relates to improvements in self-injecting syringes and aspirating syringes, and to the production of a combined self-injecting and aspirating syringe.

BACKGROUND ART

The following patents disclose various types of self-injecting syringes: U.S. Pat. No. 98,478, granted Jan. 4, 1870, to Charles H. Eccleston; U.S. Pat. No. 922,331, granted May 1, 1909, to Thomas M. Quarles; U.S. Pat. No. 1,845,036, granted Feb. 16, 1932, to Herbert H. Busher; U.S. Pat. No. 1,921,034, granted Aug. 8, 1933, to Norman O. La Marche; U.S. Pat. No. 2,664,086, granted Dec. 29, 1953, to Gerald O. Transue and U.S. Pat. No. 3,605,743, granted Sept. 20, 1971, to Raul O. Arce; and U.S. Pat. No. 4,407,283, granted Oct. 4, 1983 to Francis D. Reynolds.

U.S. Pat. No. 3,224,445, granted Dec. 21, 1965, to Norman W. Melott and U.S. Pat. No. 3,583,399, granted June 8, 1971, to Anthony F. Ritsky, both disclose syringes which are adapted for performing the procedure known as "aspiration". The procedure known as "aspiration" is defined in these patenets.

Additional aspirating syringes, requiring cartridges of a special construction, are disclosed by the following U.S. Pat. Nos.: 2,554,744, granted May 29, 1951, to Niels B. Jorgensen; 2,693,184, granted Nov. 2, 1954, to Marshall L. Lockhart; 2,693,185, granted Nov. 2, 1954, to Marshall L. Lockhart; 3,045,674, granted July 24, 1962, to Samuel D. Goldberg; 3,340,872, granted Sept. 12, 1967, to Thomas S. Cox; 3,618,603, granted Nov. 9, 1971, to Myron F. Levenson; 3,766,918, granted Oct. 23, 1973, to John D. Kessel and 4,381,779, granted May 3, 1983, to Herman Margulies.

The device shown by the aforementioned U.S. Pat. No. 3,224,445 includes a plunger having an arrow-shaped barb at its forward end which enters into the piston of a cartridge. The theory of the shape is that the barb will become connected to the piston. Its purpose is to connect together the plunger and the piston so that when a plunger is pulled rearwardly, the piston will move rearwardly with it. The barb 42 is not constructed to in any way cause the forward portion of the piston to become distorted, for providing automatic aspiration when pressure is removed from the plunger. In practice it has been found that the barb does not effectively grip the piston.

The various patents introduced above speak for themselves and therefore do not need to be specifically described in any detail. However, such patents, and the various patents cited against them, should be carefully considered for the purpose of putting the present invention into proper perspective relative to the prior art.

DISCLOSURE OF THE INVENTION

One aspect of the present invention is to provide a self-injecting syringe which is closely related to but an improvement on the self-injecting syringe disclosed by the aforementioned U.S. Pat. No. 4,407,283.

In basic construction, a self-injecting syringe of the present invention comprises a finger-grip body having an annular sidewall defining an inner chamber. A bushing is slidably received within the chamber. The bushing includes an axially extending cantilever beam which bends outwardly from a fixed end to a free end. The beam includes a radially outwardly directed lock element at its free end. When the bushing is moved rearwardly within the finger-grip body, the lock element engages a radial opening in the sidewall of the finger-grip body. A trigger carried by the body includes an inwardly directed lug which is also aligned with the opening. When the trigger is depressed, the lug enters through the opening and pushes the lock element out of engagement with the opening. This frees a compression spring which is compressed when the lock element is within the opening. The freed compression spring drives the bushing forwardly relative to the finger-grip body. As it moves, the bushing moves with it a cartridge and a hypodermic needle at the forward end of the cartridge. Such movement is attended by penetration of the needle into the tissue into which an injection is to be made.

In accordance with an aspect of the invention, the bushing includes a rearwardly projecting tubular extension which extends through the central opening provided in a rear wall portion of the finger-grip body. A handle is secured to the rear end of the bushing extension. This handle is grasped and pulled rearwardly for moving the bushing into a "cocked" position.

Preferably, a cushion stop is provided between the handle and the rear wall of the finger-grip body, to cushion the parts at the end of forward movement of the bushing. In preferred form, this cushion stop is in the form of an annular elastomeric ring located on the rearward extension of the bushing, inwardly of the handle.

In accordance with another aspect of the invention, a plunger is provided which includes a penetrator rod at its forward end which is of such a length and diameter that when it is moved into the piston in the rear portion of the syringe cartridge, it will cause a forward portion of the piston to bulge forwardly. When pressure is removed from the plunger, the forwardly bulging forward portion of the piston functions as a spring to move the penetrator rod rearwardly and at the same time enough of the distortion is relieved to cause a suction in the cartridge in an amount sufficient to produce useful aspiration.

In preferred construction, the penetrator rod is cylindrical in shape and includes a conical end with a cone angle of about 60° and a blunt or rounded front end.

In accordance with yet another aspect of the invention, the penetrator rod is sized such that its movement into the pistn will expand the piston laterally enough so that the piston will move rearwardly with the plunger when the plunger is manually pulled rearwardly. This provides a second way of creating aspiration.

These and other objects, features, characteristics and advantages pertaining to and inherent in the present invention will be apparent from the following description of a typical and therefore non-limitive embodiment of the invention.

BRIEF DESCRIPTION OF THE DRAWING

Referring to the several figures of the drawing, wherein like numerals refer to like parts throughout, and wherein:

FIG. 1 is a side elevational view of a hypodermic syringe embodying features of the present invention, such view showing the shaft of the plunger broken away, to indicate indeterminate length, and omitting a rearward portion of a thumb ring at the rearward end of the plunger;

FIG. 2 is a longitudinal sectional view of the syringe shown by FIG. 1, taken substantially along line 2—2 of FIG. 5, and showing the extendible elements of the syringe in a retracted position relative to the finger-grip body and the barrel, and showing the injection spring compressed and the releasable lock means locked, and also showing the shaft of the plunger broken away and omitting the rearward portion of the thumb ring;

FIG. 3 is a view like FIG. 2, but showing the releasable lock means released, and the cartridge and needle moved forwardly relative to the finger-grip body;

FIG. 4A is an exploded isometric view of the forward portion of the syringe that is shown by FIGS. 1-3;

FIG. 4B is an exploded isometric view of the rear portion of the syringe shown by FIGS. 1-3;

FIG. 5 is a cross-sectional view taken substantially along line 5—5 of FIG. 3;

FIG. 6 is a cross-sectional view taken substantially along line 6—6 of FIG. 3;

FIG. 7 is an enlarged scale fragmentary view in the region where the penetrator rod engages the soft rubber piston in the cartridge, such view showing the plunger in the process of being pushed forwardly into the piston, and showing the resulting distortion at the forward face of the piston;

FIG. 8 is a view like FIG. 7, but showing that when forward pressure is removed from the plunger, the front face portion of the piston functions as a spring and moves the penetrator rod and the plunger head rearwardly in position, reducing the amount of distortion at the front face of the piston;

FIG. 9 is a view like FIGS. 7 and 8, but showing the plunger in the process of being withdrawn, for the purpose of effecting additional aspiration manually;

FIG. 10 is an enlarged scale fragmentary view of the tip portion of the penetrator rod, showing a preferred penetration angle and a blunted tip; and FIG. 11 is a view like FIG. 3, but of a modified embodiment.

BEST MODE FOR CARRYING OUT THE INVENTION

Referring again to the several figures of the drawing, the illustrated embodiment 10 comprises a finger-grip body 12, a rear bushing 14, a syringe barrel 16, an injection needle 18, and a plunger 20.

The finger-grip body 12 serves as a housing for the rear bushing 14, a compression spring 22 and a releasable lock mechanism, hereinafter to be described.

Barrel 16 is essentially like the barrel 17 of the syringe shown by U.S. Pat. No. 3,583,399 and the barrel 10 of the syringe disclosed by U.S. Pat. No. 3,224,445. It includes a side loading window 26 for a cartridge 28 and opposite observation windows 30, 32. Barrel 16 is connected at its rearward end to the body 12, such as by a screw thread connection 34 and a lock nut 36.

Cartridge 28 is of conventional construction and comprises a cylindrical sidewall 38, a diaphragm wall closure 40 (FIG. 4A) at its forward end, and a piston-type closure 42 at its rearward end.

The externally threaded rear end portion 34 of barrel 16 mates with internal threaded provided at the forward end of body 12.

A slidable plunger head 44 is housed within the forward end portion of the bushing 14. It includes an axial socket 46 (FIG. 4B) sized to snugly receive a forward end portion 48 of the plunger shaft 50. A pin slot 52 is formed in a sidewall portion of the plunger head 44. A pin 54 rides within the slot 52. Pin 54 is shown in the form of a screw 54 which threads into a side opening 56 provided in the forward end portion 48 of the plunger shaft 50 (FIG. 4B). Plunger head 44 carries an axially forwardly projecting penetrator rod 58, the purpose and operation of which will hereinafter be described in some detail.

The rear end portion of plunger shaft 50 is suitably secured to a wall portion of a thumb ring 60.

In preferred form, the finger-grip body 12 is formed to include an inner chamber 62 which may be cylindrical in shape and which extends longitudinally of the body 12. Body 12 comprises an annular sidewall 64, a forward end 66 and a rearward end 68.

Finger-grip body 12 includes a radial wall 70 at its rearward end, including a central opening 72 (FIG. 4B) through which a rearward extension portion 74 of the bushing 14 extends.

Bushing 14 is formed to include a radial shoulder 16 which is directed towards, and spaced axially from, the end wall 70. A compression spring 78 surrounds busing portion 74, and includes a forward end which contacts the shoulder 76 and a rearward end which contacts the end wall 70. Compression spring 78 normally wants to bias the bushing 14 into a forward position within the body 12.

Bushing 14 is formed to include an axial slot 80 along one side. Body 12 includes a radially inwardly projecting locator pin 82, the inner end of which is located within the slot 80. Locator pin 82 allows the bushing 14 to move axially relative to the body 12 but prevents it from rotating in position relative to the body 12.

A lock beam 24 is machined out of a sidewall portion of the bushing 14. Beam 24 is in the nature of a cantilever beam (See FIG. 4B). Slots 86 are cut in the bushing 14 on opposite sides of the beam 24. A portion of the beam 24 is thinned by machining, to control the flexible action of the beam 24.

Beam 24 includes a radially outwardly projecting lock element 88 at its rearward or free end. Body 12 is formed to include a radial opening 90 positioned to be in the slide path of lock element 80. The use of the slot 80 and the locator pin 82 serves to keep the slide path of lock element 88 aligned with the opening 90. When the beam 24 is within its rest position, it extends radially outwardly as it extends rearwardly from its fixed end to its free end. Thus, when the lock element 88 comes in registry with the radial opening 90, the spring energy in the beam 24 moves the lock element 88 into a locking engagement with the opening 90.

A "cocking" handle 92 is secured to the rear end of bushing 14. In preferred form, the rear end of bushing portion 74 is externally threaded. The handle 92 is in the form of a "nut" which includes an internally threaded central opening by which it makes threaded engagement with the threads on the bushing part 74. In this manner, the bushing 14 can be easily moved into a "cocked" position by the user grabbing the handle 92 and pulling rearwardly on it. This causes a rearward movement of bushing 14 within body 12 until the lock element 88 snaps into the opening 90. As shown by FIG. 2, the rearward movement of the bushing 14 causes the compression spring 78 to be compressed.

Body 12 includes a trigger recess 94, radially outwardly from the opening 90. The recess 94 includes end walls 96, 98 at its opposite ends. A trigger 100 sets down into the recess 94. Trigger 100 includes a radially inwardly projecting operator lug 102 which is in alignment with the opening 90. The opposite ends of trigger 100 are formed to include radially elongated slots 104. These slots are closed at their opposite ends. Locator pins 106 are carried by the end walls 96, 98. These pins 106 may be in the form of screws which screw into threaded openings provided in the end walls 96, 98. The inner ends of the screws 106 project into the slots 104. This arrangement enables the trigger 100 to move radially in and out within the confines of the slots 104.

In preferred form, the finger-grip body is sculptured such that the outside of the body progressively decreases in diameter as it extends from its ends to its middle. The outer surface of the trigger 100 is sculptured in a similar manner.

When the syringe is being used, the user positions the sculptured portion of the body 12 between his or her middle and index fingers, with the trigger 100 resting against one of the fingers. As can be easily seen, when the two fingers are slightly squeezed together, the trigger 100 will be depressed. As the trigger 100 moves inwardly, the lug 102 moves radially inwardly through the opening, against the lock element 88 and moves the lock element 88 out from locking engagement with the opeing 90. As soon as lock element 88 is moved free of opening 90, the compression spring 78 is free to function. The spring energy in it is quickly released and such energy causes the bushing 14 to be rapidly propelled forwardly relative to the body 12. In preferred form, a cushion stop is provided at the end of travel of the bushing 14. The stop may be in the form of an elastomeric O-ring 110 which may surround bushing 14 at the forward end of handle 92. As shown by a comparison of FIGS. 2 and 3, when the trigger mechanism is released, the bushing 14 moves forwardly until the cushion ring 110 has made contact with the end wall 70.

The forward end of syringe barrel 16 may be internally threaded at 112, to receive threads 114 provided on a retainer nut 116. As shown by FIGS. 2 and 3, the retainer nut 116 presents a rear end surface which provides an abutment for a compression spring 118. The opposite end of compression spring 118 rests on a shoulder 120 that is formed on a second bushing 122. Bushing 122 includes a socket 124 at its rearward end which is sized to receive the forward end portion 126 of the cartridge 28. The forward end of bushing 122 includes a reduced diameter portion 128 which is externally threaded and onto which a needle base 130 is threaded. Bushing 122 includes an axial opening (FIG. 4A) through which a rearward portion 134 of the hypodermic needle 18 projects. As is well-known per se, when the needle 18 is installed onto the bushing 122, and the needle base 130 is screw tightened, the rearward extending portion 134 of the needle 18 is moved through the closure diaphragm 40 provided at the forward end of the cartridge 38.

The spring 118 wants to normally bias the bushing 122 in the rearward direction. An axial slot 136 may be formed in the forward end portion of barrel 16. This slot 136 is closed at its rearward end. Slot 136 receives a radially outwardly extending pin 138 carried by bushing 122. Thus, spring 118 can urge bushing 122 rearwardly until the pin 138 contacts the end wall of slot 136.

The "aspiration" feature of the invention will now be described. "Aspiration" in this context means the introduction of a partial vacuum in the injection cartridge after the injection needle 18 is in place in the tissue of the patient, such that if the needle 18 has inadvertently penetrated a blood vessel, blood will be drawn through the needle 18 into the cartridge 28 and will shown as a red streak.

A standard injection cartridge, such as cartridge 28 shown in FIGS. 1–3 and 4A, has a soft rubber piston 42 inside of a glass cylinder 38 which contains the fluid to be injected. According to one aspect of the present invention, means is provided for automatically deflecting and distorting the working face 43 of the rubber piston 42 to produce first a positive pressure then a negative pressure in said cylinder 38, while simultaneously gripping the rubber piston 42 to permit manual aspiration, by pulling the piston back in the cartridge to any degree.

As shown by FIGS. 2, 3, and 7–9, a unique aspirating penetrator rod 58 is provided integral with the plunger assembly 20 that is used to push the rubber piston 42 in the cartridge 28 to inject fluid out through the needle 18. In the illustrated embodiment, the penetrator rod 58 is secured to the plunger head 44. The aspirating penetrator 58 has a semi-sharp end such that it will enter the rubber piston readily. The length of the aspirating penetrator rod 58 is equal to or slightly greater than the length of the rubber piston 42, such that when the penetrator rod 58 is fully inserted, the working face 43 is distorted in a domed or cone form, approximately as illustrated in FIG. 7. The penetrator rod length is not great enough for the tip of the penetrator rod 58 to pierce completely through the rubber piston 42. The length of the penetrator rod 58 can be greater without piercing through if the point or tip of the penetrator is slightly blunted, as shown. The volume of fluid displaced by the distortion of the working face 43 of the rubber piston 42 is forced out of the needle along with fluid displaced by linear movement of the piston as a whole. Any time the injection force of the piston rod 50 is applied and then removed, as illustrated in FIG. 8, the inherent resiliency of the forward face portion of rubber piston 42 partially pushes back the penetrator rod 58, allowing the working face 43 of the rubber piston 42 to reacquire a more nearly planar surface. The reduction in volume due to the partial elimination of the piston-face distortion (while the friction between the piston 42 and the glass cylinder 38 prevents the piston from moving as a whole) induces a negative pressure in the fluid, providing aspiration as described. In FIG. 8, the amount of distortion elimination of the piston-face is labeled "x". The former bulged shape is shown by a broken line.

The diameter of the penetrator rod 58 is large enough to expand the rubber piston laterally so as to increase the friction between the piston 42 and the glass cylinder 38 and large enough to require signigicant force to withdraw the penetrator rod 58 from the rubber piston 42. Tests have shown that the cone angle of the penetrator tip is important to proper operation of the device. A 60° total tip or cone angle, as illustrated in FIG. 10, has proven to be a good choice.

If the user of a syringe equipped with this aspiration feature wishes more aspiration than that which would be automatically provided as desribed, the user has but to manually pull back on the piston rod 50 a small amount (FIG. 9). The penetrator rod 58, if properly sized, will remain in the rubber piston 42 and will pull the piston 42 back along the walls of the cartridge chamber 38, creating as much aspiration or increased volume differential as desired. FIG. 9 shows a rearward pulling movement of the piston rod 50, and a linear travel of the front face 43 of the piston 42, a displacement amount "y".

A use of the syringe will now be described:

Starting with the various components of the syringe 10 positioned as shown in FIG. 3, but without a cartridge 28 in the chamber, the driving mechanism within the body 12 can be retracted by the user first grasping the handle 92 and using it to pull the bushing 14 rearwardly, followed by the user pulling rearwardly on the ring 60 in order to pull the plunger head 44 and the penetrator rod 58 back into the bushing 14. Of course, the bushing 14 will move rearwardly until the locking element 88 enters and becomes engaged in the opening 90. A cartridge is installed through the window 26. The front end 126 of the cartridge is inserted into the socket 124 while the cartridge 28 is at an angle with respect to the barrel 16. The user then pushes forward on the cartridge, causing the bushing 122 to move forward against the force of spring 118. The rear of the cartridge 28 is then swung inwardly so as to set the cartridge into the barrel 16. The plunger 20 is then moved forwardly to cause the penetrator rod 58 to enter into the piston 42. With a cartridge 28 within the barrel chamber, and the parts in their "cocked" position, the syringe 10 is now ready to use.

Prior to injection, the middle index fingers of the user are positioned on opposite sides of the body wall 64. One finger is loosely positioned on the trigger 100 and the other finger is positioned diametrically opposite the body 12. The thumb is loosely placed within the thumb ring 60. Next, the needle point 18 is set against the particular tissue into which an injection is to be made. The user then applies a gentle squeezing pressure on the trigger 100 by moving the two fingers together. This squeezing movement causes the fingers to depress the trigger 100 an amount sufficient to dislodge lock element 88 from radial opening 90. When this happens, stored energy within the compression spring 22 is freed to act against the bushing 14. Extension of this spring 22 is immediate and quick and results in a fast forward movement of the bushing 14, the cartridge 30, the needle 18 and the bushing 122, all relative to the body 12 and the barrel 16. This movement is attended by a piercing of the needle point into the tissue. Bushing 14 and the parts carried thereby are moved forwardly until the bushing movement is stopped by cushioning ring 110 meeting end wall 70. Any additional penetration of the needle 18 that might be necessary is accomplished by the user merely pushing the entire syringe towards the tissue until sufficient additional penetration is achieved.

The use of the aspirating feature has already been described and will not be repeated other than to say that aspiration is practiced following penetration and before thumb pressure is used for moving the plunger rod 20 forwardly for the purpose of injecting the fluid that is within the cartridge 20 through the needle and into the patient.

The various parts of the syringe can be constructed from metal or plastic materials, in accordance with the state of the art at the time of construction of a particular syringe. The various parts may be secured together in any simple manner as long as those parts which must be separated can be separated.

In another embodiment (FIG. 11), the bushing 14' could be constructed to extend forwardly and be at its forward end connected to the forward bushing. In this embodiment the single bushing would define the barrel for the cartridge. A support structure would extend forwardly from the finger-grip body to provide a support for the forward portion of such bushing. This latter part could terminate in the form of a ring 140 surrounding the needle mount 128. An advantage of this construction is that it would make it possible to eliminate structure from around the base 130 of the needle 18, thereby reducing the overall size of the forward end of the syringe. This would make it easier for the user to see into a patient's mouth, when the syringe is used to dental work.

The invention and its attendant advantages will be understood from the foregoing description of a typical and preferred embodiment, constituting the best mode of the invention known to applicant at the time of filing the patent application. However, it will be apparent from the embodiment, and from the following claims, that various changes may be made in the form, construction, and arrangement of the parts of the syringe without departing from the spirit and scope of the invention. Accordingly, I do not wish to be restricted to the specific form shown, or to the specific use mentioned, except to the extent that the invention is defined in the following claims.

What is claimed is:

1. A self-injecting hypodermic syringe of a type for handling a cartridge which is attachable to a needle at its forward end and which includes a piston at its rearward end, said syringe comprising:

a finger-grip body having a forward end and a rearward end, an annular sidewall defining an axial bushing chamber within said body and an outer grip portion adapted to be gripped between two fingers of a user, a radial opening in said sidewll, and an end wall at the rearward end of said body, including a central opening;

a syringe barrel having a rearward end connected to the forward end of said body, a forward end, and a cartridge receiving chamber between said ends;

a tubular bushing slidably received within said bushing chamber, and movable between a rearward position and a forward position in said bushing chamber, said bushing including a forward cartridge contacting end, and a rearwardly directed should means spaced axially from said end wall;

a compression spring within said bushing chamber having a forward end in contact with said shoulder means and a rearward end in contact with said end wall, said compression spring normally biasing said bushing into its forward position, and said spring being compressed when the bushing is in its rearward position;

said bushing carrying a leaf spring at a side location, said leaf spring having a fixed end connected to the bushing and a free end, said leaf spring extending axially of the bushing and normally extending radially outwardly as it extends from its fixed end to its free end, said leaf spring carrying a radially outwardly directed lock element;

said lock element being positioned such that upon a rearward movement of the bushing within the body, to compress the spring, the lock element will engage the radial opening, to in that manner lock the bushing in position relative to the body, and hold the spring in a compressed condition while so locked, said bushing being in its rearward position when the lock element is in the radial opening;

trigger means carried by said finger-grip body, operable to be moved radially inwardly by finger pressure, and including operator means positioned such that when the trigger is so moved the operator means will contact the leaf spring and move the lock element radially inwardly of the body, to in that manner disengage it from the radial opening, to free the compression spring so that the spring energy within the compression spring can act to propel the bushing, the cartridge and the needle axially forwardly relative to the finger-grip body; and a plunger including a plunger rod which extends axially through said bushing and includes a forward end contactable with a piston within a cartridge, and a rearward end including means for receiving thumb pressure for moving the plunger rod forwardly against the piston within the cartridge, for moving the piston forwardly within the cartridge.

2. A syringe according to claim 1, wherein said body includes a trigger recess bounded at its ends by wall portions of said body, wherein said trigger means is located within said recess and includes opposite ends having radially elongated slots closed at their ends, and said body includes locator pins extending into the slots, said slots and said pins mounting said trigger means for a limited amount of radial movement.

3. A syringe according to claim 2, wherein the operator means of said trigger means is a lug in alignment with the radial opening in said body, so that when the trigger means is depressed the lug will be moved against the lock element and push it inwardly out of engagement with said openings.

4. A syringe according to claim 1, wherein the leaf spring is an integral part of the tubular bushing and is machined from a sidewall portion of the bushing.

5. A syringe according to claim 1, wherein the tubular bushing has a rearwardly extending portion which extends through the central opening in the end wall at the rearward end of the finger-grip body, and handle means on said bushing rearwardly of said end wall, by which said bushing can be gripped and pulled rearwardly to set the lock element into the radial opening.

6. A syringe according to claim 5, comprising shock absorber means between said handle and said end wall positioned to provide a cushion between the handle and the end wall during forward movement of the bushing.

7. A syringe according to claim 6, wherein the rearward end of the bushing is externally threaded and the handle is in the form of a nut and it includes threads which engage the threads on the bushing.

8. A syring according to claim 7, comprising shock absorber means in the form of an elastomeric ring surrounding said bushing between the handle and the end wall.

9. A syringe according to claim 1, comprising a member at the forward end of the plunger rod which is movable axially relative to the plunger rod, between a forward position and a rearward position, said member including a penetrator rod which extends axially forwardly from the member and is constructed to extend into the piston within a cartridge, said member being sized to cause a forward portion of the piston to bulge forwardly in response to the member being inserted into the piston.

10. In a self-aspirating syringe of a type which includes a tubular bushing that is housed within a finger-grip body, and which by finger pressure actuation of a trigger carried by the body is driven forwardly by a spring against a cartridge, for rapidly moving the cartridge and a needle at the forward end of the cartridge forwardly relative to the body, to cause a rapid penetration of the needle into a tissue of a patient, the improvement comprising:

said finger-grip body including an annular sidewall, defining an axial bushing chamber within said body, and an outer grip portion adapted to be gripped between two fingers of a user, a radial opening in said sidewall, and an end wall at the rearward end of said body, including a central opening;

a tubular cartridge contacting and moving the bushing slidably received within said bushing chamber, and movable between a rearward position and a forward position in said bushing chamber, said bushing including a forward cartridge contacting end and a rearwardly directed shoulder means spaced axially from said end wall;

a compression spring within said bushing chamber having a forward end in contact with said shoulder means and a rearward end in contact with said end wall, said compression spring normally biasing said bushing into its forward position, and said spring being compressed when the bushing is in its retracted position;

said bushing carrying a leaf spring at a side location, said leaf spring having a fixed end connected to the bushing and a free end, said leaf spring extending axially of the bushing and normally extending radially outwardly as it extends from its fixed end to its free end, said leaf spring carrying a radially outwardly directed lock element;

said lock element being positioned such that upon a rearward movement of the bushing within the body, to compress the spring, the lock element will engage the radial opening, to in that manner lock the bushing in position relative to the body, and hold the spring in a compressed condition while so locked, said bushing being in its rearward position when the lock element is in the radial opening; and trigger means carried by said finger-grip body, operable to be moved radially inwardly by finger pressure, and including operator means positioned such that when the trigger is so moved the operator means will contact the leaf spring and move the lock element radially inwardly of the body, to in that manner disengage it from the radial opening, to free the compression spring so that the spring energy within the compression spring can act to propel the bushing, the cartridge and the needle axially forwardly relative to the finger-grip body.

11. A syringe according to claim 10, further including a plunger rod which extends axially through said bushing, means at the forward end of the plunger rod contactable with a piston within a cartridge, and a rearward end including means for receiving thumb pressure for moving the plunger rod forwardly through the bushing and against the piston within the cartridge, for moving the piston forwardly within the cartridge.

12. A syringe according to claim 10, wherein said body includes a trigger recess bounded at its ends by wall portions of said body, wherein said trigger means is located within said recess and includes opposite ends having radially elongated slots closed at their ends, and said body includes locator pins extending into the slots, said slots and said pins mounting said trigger means for a limited amount of radial movement.

13. A syringe according to claim 2, wherein the operator means of said trigger means is a lug in alignment with the radial opening in said body, so that when the trigger means is depressed the lug will be moved against the lock element and push it inwardly out of engagement with said openings.

14. A syringe according to claim 10, wherein the leaf spring is an integral part of the bushing housing and is machined from a sidewall portion of the bushing.

15. A syringe according to claim 1, wherein the tubular bushing has a rearwardly extending portion which extends through the central opening in the end wall at the rearward end of the finger-grip body, and handle means on said bushing rearwardly of said end wall, by which said bushing can be gripped and pulled rearwardly to set the lock element into the radial opening.

16. A syringe according to claim 15, comprising shock absorber means between said handle and said end wall positioned to provide a cushion between the handle and the end wall during forward movement of the bushing.

17. A syringe according to claim 16, wherein the rearward end of the bushing is externally threaded and the handle is in the form of a nut and it includes threads which engage the threads on the bushing.

18. A syringe according to claim 17, comprising shock absorber means in the form of an elastomeric ring surrounding said bushing between the handle and the end wall.

19. In a hypodermic syringe of a type which includes means for supporting a cartridge of a type having a forward end that is connectable to a needle, a cylindrical body, and an elastomeric, solid-center piston constitutng a rear closure for the cartridge and which is slidably received within the cylindrical body, and a plunger which is moved forwardly against the rear of the piston for pushing the piston through the cartridge body, to in that manner move fluid out from the cartridge through the needle, and aspiration means comprising:

an axially forwardly extending penetrator rod at the forward end of the plunger, such penetrator rod having a tapering, bluntly pointed tip and being of such a length that it will penetrate into and through all but a relatively thin forward portion of the solid-center piston, when the penetrator rod is pushed into the piston, and which will bow such forward portion of the piston forwardly when pushed into the piston, such that when pressure is removed from the plunger such forwardly bowed portion of the piston will function like a spring to move the penetrator rod rearwardly an amount sufficient to relieve the forward bulging distortion of such piston portion an amount sufficient to cause a useful aspirating suction in the cartridge, and wherein the penetrator rod is supported to move rearwardly in response to the spring action of the forwardly bulging portion of the piston when the plunger force is removed from it, so that aspiration will occur automatically.

20. A hypodermic syringe according to claim 19, wherein the penetrator rod is sized such that it will sufficiently grip the piston by an amount sufficient so that upon a manual rearward movement of the plunger the piston will move rearwardly with the penetrator rod, to provide additional aspirating suction in the cartridge.

21. A hypodermic syringe according to claim 19, wherein the penetrator rod has a substantially cylindrical shank and the bluntly pointed tip tapers from said shank to a generally rounded end.

22. A hypodermic syringe according to claim 21, wherein the taper occurs at an angle of about 60°.

23. A hypodermic syringe according to claim 19, wherein a socket member is connected to the end of the penetrator rod opposite the bluntly pointed tip, and the plunger includes an end portion which extends into said socket, and there is a connection between the plunger and the socket member which allows the plunger to be moved rearwardly in short distance without exerting a force on the socket member, and then additional rearward movement of the plunger will exert a pulling force on the socket member.

24. A hypodermic syringe according to claim 23, wherein the penetrator rod has a substantially cylindrical body and the bluntly pointed tip tapers from said body to a generally rounded end.

25. A hypodermic syringe according to claim 23, wherein the penetrator rod is sized such that it will sufficiently grip the piston by an amount sufficient so that upon a manual rearward movement of the plunger the piston will move rearwardly with the penetrator rod, to provide additional aspirating suction in the cartridge.

* * * * *